(12) United States Patent
Fujita et al.

(10) Patent No.: US 9,598,345 B2
(45) Date of Patent: Mar. 21, 2017

(54) METHOD FOR PRODUCING UNSATURATED ACID ESTER OR UNSATURATED ACID

(71) Applicant: ASAHI GLASS COMPANY, LIMITED, Chiyoda-ku (JP)

(72) Inventors: Tomoyuki Fujita, Tokyo (JP); Koichi Murata, Tokyo (JP); Naoko Shirota, Tokyo (JP); Yusuke Suzuki, Tokyo (JP); Daisuke Jomuta, Tokyo (JP)

(73) Assignee: ASAHI GLASS COMPANY, LIMITED, Chiyoda-ku (JP)

( * ) Notice: Subject to any disclaimer, the term of this patent is extended or adjusted under 35 U.S.C. 154(b) by 0 days.

(21) Appl. No.: 14/991,393

(22) Filed: Jan. 8, 2016

(65) Prior Publication Data

US 2016/0122279 A1    May 5, 2016

Related U.S. Application Data

(63) Continuation of application No. PCT/JP2014/067940, filed on Jul. 4, 2014.

(30) Foreign Application Priority Data

Jul. 12, 2013 (JP) .................. 2013-146864

(51) Int. Cl.
*C07C 67/10* (2006.01)
*C07C 67/00* (2006.01)
*C07C 51/093* (2006.01)

(52) U.S. Cl.
CPC ............ *C07C 67/10* (2013.01); *C07C 51/093* (2013.01); *C07C 67/00* (2013.01)

(58) Field of Classification Search
None
See application file for complete search history.

(56) References Cited

U.S. PATENT DOCUMENTS

| | | | |
|---|---|---|---|
| 2,226,645 A | 12/1940 | Thomas et al. | |
| 2,438,164 A | 3/1948 | Harrington et al. | |
| 3,857,882 A * | 12/1974 | Auer ................ | C07C 51/377 562/599 |

FOREIGN PATENT DOCUMENTS

| | | |
|---|---|---|
| JP | 47-9019 | 5/1972 |
| JP | 48-64018 | 9/1973 |
| JP | 49-18823 | 2/1974 |
| JP | 56-118038 | 9/1981 |
| WO | WO 2014/038489 A1 | 3/2014 |

OTHER PUBLICATIONS

International Search Report issued Sep. 16, 2014 in PCT/JP2014/067940 filed Jul. 4, 2014 (with English translation).

Written Opinion issued Sep. 16, 2014 in PCT/JP2014/067940 filed Jul. 4, 2014.

Ch. Weizmann, et al., "The Synthesis of α-Alkoxyisobutyric Acids and Alkyl Methacrylates from Acetonechloroform", J. Am. Soc., vol. 70, 1948, 6 pgs.

Lynette M. Oh, et al., "Development of a Scalable Synthesis of GSK183390A, a PPAR α/γ Agonist", Organic Process Research & Development, vol. 11, (6), 2007, 11 pgs.

Bruce L. Jenesen, et al., "Novel Acid-Catalyzed Rearrangement of 2, 2-Dihaloethanols, A 1,2-Halogen Shift Affording α-Haloketones", Tetrahedron Lett., (31), 1977, 4 pgs.

Donald G. Kundiger, et al., "The Rearrangement of Certain Trichloromethylcarbinols to α-Chloro Acide Chlorides", J. Am. Chem. Soc., 1960, 4 pgs.

Sh. A. Saghatelyan, et al., "The reaction of trihalo-tert-butanols with bases in ether and in aqueous and alcoholic media", Khimicheskii Zhurnal Armenii, Issue 1-2, vol. 53, 2000, 8 pgs. (with English Abstract).

* cited by examiner

*Primary Examiner* — Yong Chu
*Assistant Examiner* — Ana Z Muresan
(74) *Attorney, Agent, or Firm* — Oblon, McClelland, Maier & Neustadt, L.L.P.

(57) ABSTRACT

The present invention relates to a method for producing an unsaturated-acid ester or an unsaturated acid, containing a step of reacting a compound (1) represented by the following formula (1) with a compound represented by the following formula (2) (excluding the compound (1)) in the presence of a Lewis acid catalyst at a temperature of the boiling point of the compound (1) or higher and 350° C. or lower, thereby obtaining products including a compound represented by the following formula (3):

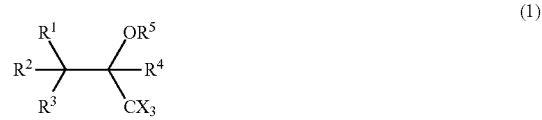

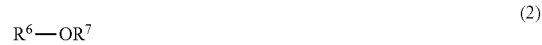

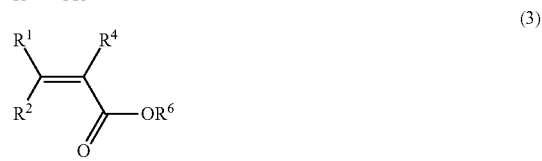

(in formula (1) and formula (3), $R^1$, $R^2$ and $R^4$ each independently may be hydrogen atom or an alkyl group, $R^3$ and $R^5$ each independently are hydrogen atom or a deuterium atom, and X is a halogen atom; in formula (2) and formula (3), $R^6$ may be hydrogen atom, an alkyl group or an aryl group, and $R^7$ is hydrogen atom or a deuterium atom).

15 Claims, No Drawings

METHOD FOR PRODUCING UNSATURATED ACID ESTER OR UNSATURATED ACID

TECHNICAL FIELD

The present invention relates to a method for producing an unsaturated-acid ester or unsaturated acid.

BACKGROUND ART

Industrially widely used as a method for producing methacrylic acid and methyl methacrylate is the ACH method (acetone cyanohydrin method), in which methacrylic acid and/or methyl methacrylate is produced from acetone and hydrocyanic acid (hydrogen cyanide).

However, hydrocyanic acid is highly toxic, and use thereof is undesirable.

Known as methods in which hydrocyanic acid is not used include, for example, a method in which isobutene or tertiary butyl alcohol is oxidized and a method in which propionic acid or a propionic acid ester is reacted with formaldehyde or the like.

However, isobutene is in a C4 fraction from ethylene plants or cracking gasoline plants, and there are limitations in procuring the compound for use as a material for methyl methacrylate production. In addition, it can be produced only in places equipped with a naphtha cracker.

In the method for production from propionic acid, the conversion to methyl methacrylate is low and the catalyst life is short. In addition, the Pd complex used as a catalyst for obtaining propionic acid from ethylene is not easy to synthesize and the stability thereof is problematic.

Meanwhile, also known is a method in which methacrylic acid or a methacrylic acid ester is obtained from a 1,1,1-trihalo-2-methyl-2-propanol. For example, a method is known in which 2-methoxy-2-methylpropanoic acid is obtained from 1,1,1-trichloro-2-methyl-2-propanol and the methyl ester thereof is obtained, and then subjected to alcohol elimination to obtain methyl methacrylate (Non-Patent Document 1).

In this method, however, it is necessary for obtaining 2-methoxy-2-methylpropanoic acid that a basic compound should be used in an amount at least 3 times by mole the amount of the starting-material alcohol. In addition, when methyl methacrylate is obtained from the methyl 2-methoxy-2-methylpropanoic acid, it is necessary that a phosphorus compound, metal chloride or the like should be used in an amount not less than an equivalent amount. The method is hence not considered to be an industrially practicable production method. Moreover, although the chlorine moiety in the starting material becomes a salt with the basic compound, it is difficult to effectively utilize the salt as such.

Known as another method for producing methacrylic acid is a method in which 2-chloro-2-methylpropanoic acid is heated at from 250° C. to 600° C. in the presence of a catalyst such as calcium chloride (Patent Document 1). Known as a method for producing methyl methacrylate is a method in which methyl 2-chloro-2-methylpropanoate is heated as a starting material at from 480° C. to 550° C. without a catalyst and then heated at from 250° C. to 350° C. in the presence of a dehydrohalogenation catalyst such as a metal chloride (Patent Document 2). The 2-chloro-2-methylpropanoic acid and the methyl 2-chloro-2-methylpropanoate can be produced, for example, by a method in which 2-bromo-2-methylpropanoic acid is obtained by reacting 1,1,1-tribromo-2-methyl-2-propanol with potassium hydroxide (Non-Patent Document 2).

In these methods, however, it is necessary to use a basic compound in an amount at least two times by mole the amount of the starting-material alcohol. In addition, the halogen salts obtained are difficult to be used effectively.

PRIOR ART DOCUMENTS

Patent Documents

Patent Document 1: JP-A-S48-64018
Patent Document 2: JP-A-S49-18823

Non-Patent Documents

Non-Patent Document 1: J. Am. Chem. Soc. (1948), Vol.70, pp. 1153-1158
Non-Patent Document 2: Khimicheskii Zhurnal Armenii (2000), Vol.53(1-2), pp. 99-104, English abstract; CAN 134:41908

SUMMARY OF THE INVENTION

Problems that the Invention is to Solve

An object of the present invention is to provide a method for producing an unsaturated-acid ester or an unsaturated acid on an industrial scale without using any highly toxic compound and without using a large amount of a chemical such as a basic compound.

Means for Solving the Problems

The present invention relates to a method for producing an unsaturated-acid ester or an unsaturated acid, described the following (1) to (7).

(1) A method for producing an unsaturated-acid ester or an unsaturated acid, containing a step of reacting a compound (1) represented by the following formula (1) with a compound (2) represented by the following formula (2) (excluding the compound (1)) in the presence of a Lewis acid catalyst at a temperature of the boiling point of the compound (1) or higher and 350° C. or lower, thereby obtaining products including a compound (3) represented by the following formula (3):

[Chem. 1]

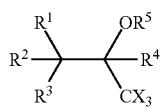

(1)

(in formula (1), $R^1$, $R^2$, and $R^4$ each independently are a hydrogen atom, a deuterium atom, or an alkyl group which has a carbon number of from 1 to 3 and may have been substituted with a halogen atom and/or a deuterium atom, $R^3$ and $R^5$ each independently are a hydrogen atom or a deuterium atom, and X is a chlorine atom, a fluorine atom, a bromine atom, or an iodine atom);

$$R^6-OR^7 \qquad (2)$$

(in formula (2), $R^6$ is a hydrogen atom, a deuterium atom, an alkyl group which has a carbon number of from 1 to 11 and may have been substituted with a halogen atom and/or a deuterium atom, or an aryl group which has a carbon number of from 1 to 11 and may have been substituted with a halogen atom and/or a deuterium atom, and $R^7$ is a hydrogen atom or a deuterium atom); and

[Chem. 2]

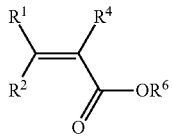

(3)

(in formula (3), $R^1$, $R^2$, and $R^4$ are the same as defined above with regard to formula (1), and $R^6$ is the same as defined above with regard to formula (2)).

(2) The method for production according to the above-mentioned (1), in which the Lewis acid catalyst is any of compounds represented by the following formula (4) or a mixture of these.

$$M_n Y_m \quad (4)$$

(in formula (4), M is a cation of hydrogen or a metal or metalloid selected from the group consisting of elements of Group 2 and Groups from 4 to 14 of the periodic table, Y is an anion selected from the group consisting of oxide ions, halide ions, a sulfate ion, a nitrate ion, a carbonate ion, a hydrogen carbonate ion, a sulfide ion, a hydroxide ion, alkoxide ions, a phosphate ion, an acetate ion, and a perchlorate ion, and n and m are numbers satisfying (valence of the cation M)×n=(valence of the anion Y)×m).

(3) The method for production according to the above-mentioned (2), in which the M is a cation of a metal or metalloid selected from the group consisting of zinc, zirconium, silicon, chromium, iron, aluminum, lead, magnesium, indium, cobalt, manganese, and nickel.

(4) The method for production according to the above-mentioned (2) or (3), in which the Y is an oxide ion.

(5) The method for production according to the above-mentioned (1), in which the Lewis acid catalyst is a solid acid.

(6) The method for production according to the above-mentioned (5), in which the solid acid is at least one member selected from the group consisting of activated clay, acid clay, zeolites, heteropolyacids, and ion-exchange resins.

(7) The method for production according to any one of the above-mentioned (1) to (6), in which the reaction is conducted in a gas phase.

Effects of the Invention

According to the present invention, an unsaturated-acid ester or an unsaturated acid can be produced on an industrial scale without using any highly toxic compound and without using a large amount of a chemical such as a basic compound.

MODES FOR CARRYING OUT THE INVENTION

In this description, a compound represented by formula (1) is referred to as "compound (1)", a compound represented by formula (2) (excluding the compound (1)) is referred to as "compound (2)", and a compound represented by formula (3) is referred to as "compound (3)".

Furthermore, in this description, methacrylic acid is also called "MAA", methyl methacrylate is also called "MMA", and 1,1,1-trichloro-2-methyl-2-propanol is also called "TCMP".

The following definition of terms holds throughout the description and the claims.

The term "Lewis acid" means an electron pair acceptor, and is a conception which includes Brønsted acids.

The term "Brønsted acid" means a proton donor.

The term "solid acid" means a substance which is solid and shows acid nature.

"Batch mode" is a mode of reaction in which starting materials and a catalyst are introduced into any desired reaction vessel and are allowed to react for a given time period at a given reaction temperature and the resultant reaction products are taken out at a time. Small-amount treatments are possible, and the reaction time, reaction temperature, amounts to be reacted, and the like can be changed at will.

"Continuous mode" is a mode of reaction in which starting materials are continuously fed at a given rate to a catalyst layer in any desired atmosphere and are allowed to reside in the layer for a given time period to react, to thereby continuously produce a reaction product. Since large-quantity production is possible through a continuous operation, this mode is suitable for industrialization.

The term "boiling point" means boiling point measured at ordinary pressure (1 atm; 101,325 Pa).

The method of the present invention for producing an unsaturated-acid ester or an unsaturated acid contains a step of reacting a compound (1) with a compound (2) in the presence of a Lewis acid catalyst at a temperature of the boiling point of compound (1) or higher and 350° C. or lower, thereby obtaining products including compound (3).

The present invention is explained below in detail.
Compound (1)

In the present invention, the compound (1) is used as one of the starting materials.

The compound (1) is a compound represented by the following formula (1).

[Chem. 3]

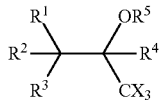

(1)

(In formula (1), $R^1$, $R^2$ and $R^4$ each independently are a hydrogen atom, a deuterium atom, or an alkyl group which has a carbon number of from 1 to 3 and may have been substituted with a halogen atom and/or a deuterium atom, $R^3$ and $R^5$ each independently are a hydrogen atom or a deuterium atom, and X is a chlorine atom, a fluorine atom, a bromine atom, or an iodine atom.)

Examples of the alkyl group which has a carbon number of from 1 to 3 and may have been substituted with a halogen atom and/or a deuterium atom include a methyl group, an ethyl group and a propyl group, and these groups in which at least one of the hydrogen atoms has been replaced with a halogen atom and/or a deuterium atom.

It is preferable that $R^1$, $R^2$, and $R^4$ should each independently be a hydrogen atom, a deuterium atom, or an alkyl group which has a carbon number of from 1 to 3 and may have been substituted with a deuterium atom.

R³ preferably is a hydrogen atom or a deuterium atom.

More preferred of the compounds according to the definition are compounds in which R¹ to R³ each independently are a hydrogen atom or a deuterium atom and R⁴ is a methyl group in which any of the hydrogen atoms may be a deuterium atom.

The compound (1) may be in the form of a hydrate thereof, etc.

The compound (1) to be used in the present invention may be a commercial product, or may be one synthesized from other compounds.

Examples of methods for synthesizing from other compounds include: a method in which a ketone or an aldehyde is reacted with a trihalomethane in the presence of a basic compound (JP-A-S49-82611; U.S. Pat. No. 2,462,389; J. Org. Chem. (2000), Vol. 65, pp. 7211-7212); a method in which a ketone is electrochemically reacted with carbon tetrachloride (Tetrahedron Lett. (1986), Vol. 27(27), pp. 3129-32); and a method in which a trihaloacetoaldehyde or a trihaloacetone is reacted with an aromatic compound (J. Org. Chem. (2000), Vol. 65, pp. 1597-1599; Japanese Patent No. 3883354).

In the case where in the compound (1), R¹ to R³ each independently are a hydrogen atom or a deuterium atom and R⁴ is a methyl group which may have been substituted with a deuterium atom, it is preferred to prepare this compound (1) from acetone which may have been substituted with a deuterium atom and a halogenoform or a heavy halogenoform.

Heavy halogenoforms, in particular, heavy chloroform, are easily available as compared with deuterium cyanide, and are suitable for use as starting materials for producing deuterated unsaturated-acid eaters.

Compound (2)

In the present invention, the compound (2) is used as the other starting material.

The compound (2) is a compound represented by the following formula (2) excluding the compound (1).

$$R^6\text{—}OR^7 \quad (2)$$

(In formula (2), R⁶ is a hydrogen atom, a deuterium atom, an alkyl group which has a carbon number of from 1 to 11 and may have been substituted with a halogen atom and/or a deuterium atom, or an aryl group which has a carbon number of from 1 to 11 and may have been substituted with a halogen atom and/or a deuterium atom, and R⁷ is a hydrogen atom or a deuterium atom.)

In the case where R⁶ is an alkyl group which may have been substituted with a halogen atom and/or a deuterium atom or an aryl group which may have been substituted with a halogen atom and/or a deuterium atom, it is preferable that the number of carbon atoms thereof should be from 1 to 8.

Examples of compound (2) include water, heavy water, alcohols such as methanol, ethanol, propanol, isopropanol, butanol, isobutyl alcohol, tertiary butyl alcohol, pentanol, hexanol, cyclohexanol, heptanol, octanol, 2-ethylhexanol, phenol, benzyl alcohol, and tolyl alcohol, and those in which at least some of the hydrogen atoms in the molecule thereof have been replaced with a halogen atom and/or a deuterium atom.

Examples of the alcohols substituted with a halogen atom (halogen-substituted alcohols) include 2,2,2-trichloroethanol, 2,2,3,3-tetrafluoropropanol, 1,1,1,3,3,3-hexafluoro-2-propanol, and fluoroalkyl alcohols represented by the general formula $C_pF_{2p+1}(CH_2)_qOH$ (p is an integer of from 1 to 8, and q is an integer of from 1 to 3). Specific examples of the $C_pF_{2p+1}(CH_2)_qOH$ include $CF_3CH_2OH$, $CF_3CF_2CH_2OH$, $CF_3CF_2CF_2CH_2OH$, $CF_3(CF_2)_3CH_2OH$, $CF_3(CF_2)_5CH_2OH$, $CF_3CF_2CH_2CH_2OH$, $CF_3(CF_2)_3CH_2CH_2OH$, $CF_3(CF_2)_5CH_2CH_2OH$, $CF_3(CF_2)_7CH_2CH_2OH$, $CF_3CF_2(CH_2)_3OH$, $CF_3(CF_2)_3(CH_2)_3OH$, and $CF_3(CF_2)_5(CH_2)_3OH$. Preferred of these are $CF_3(CF_2)_3CH_2CH_2OH$ and $CF_3(CF_2)_5CH_2CH_2OH$.

Examples of the alcohols substituted with a deuterium atom (deuterium-substituted alcohols) include alcohols having a carbon number of from 1 to 3, in which at least a part thereof has been substituted with a deuterium atom.

Preferred of these compounds (2) are water, heavy water, methanol, ethanol, or those in which at least some of the hydrogen atoms thereof have been replaced with a halogen atom and/or a deuterium atom. More preferred is methanol which may have been substituted with a deuterium atom.

In the present invention, the amount of the compound (2) to be used is preferably from 0.5 to 20 mol, more preferably from 1 to 10 mol and most preferably from 1 to 5 mol, per 1 mol of the compound (1).

In the case where the amount of the compound (2) used is the lower limit or more, a sufficient conversion is obtained. In the case of the upper limit or less, an increase in volume efficiency is attained. Consequently, the efficiency of production of an unsaturated-acid ester or unsaturated acid improves.

In the present invention, in the case of using an alcohol as the compound (2), an unsaturated-acid ester is apt to be efficiently obtained in one step, and in the case of using water or heavy water, an unsaturated acid is apt to be efficiently obtained in one step.

Incidentally, the compound (2) may be used as a mixture with the solvent or diluent gas which will be described later.

Compound (3)

According to the present invention, the compound (3), which is an unsaturated-acid ester or an unsaturated acid, is obtained as the desired reaction product.

The compound (3) is represented by the following formula (3).

[Chem. 4]

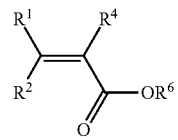

(3)

(In formula (3), R¹, R² and R⁴ are the same as defined above with regard to formula (1), and R⁶ is the same as defined above with regard to formula (2).)

Examples of R⁶ include a hydrogen atom, a deuterium atom, and a methyl group, an ethyl group, a propyl group, an isopropyl group, a butyl group, an isobutyl group, a tertiary butyl group, a pentyl group, a hexyl group, a cyclohexyl group, a heptyl group, an octyl group, a 2-ethylhexyl group, a phenyl group, a benzyl group, and a tolyl group, and these groups in which at least one of the hydrogen atoms has been replaced with a halogen atom and/or a deuterium atom.

Examples of the groups substituted with a halogen atom include a 2,2,2-trichloroethyl group, a 2,2,3,3-tetrafluoropropyl group, a 1,1,1,3,3,3-hexafluoro-2-propyl group, and fluoroalkyl groups represented by the general formula $C_pF_{2p+1}(CH_2)_q$ (p is an integer of from 1 to 8, and q is an integer of from 1 to 3). Specific examples of the $C_pF_{2p+1}(CH_2)_q$ group include a $CF_3CH_2$ group, $CF_3CF_2CH_2$ group, $CF_3CF_2CF_2CH_2$ group, $CF_3(CF_2)_3CH_2$ group, $CF_3(CF_2)_5CH_2$ group, $CF_3CF_2CH_2CH_2$ group, $CF_3(CF_2)_3CH_2CH_2$ group, $CF_3(CF_2)_5CH_2CH_2$ group, $CF_3(CF_2)_7CH_2CH_2$ group, $CF_3CF_2(CH_2)_3$ group, $CF_3(CF_2)_3(CH_2)_3$ group, and $CF_3(CF_2)_5(CH_2)_3$ group. Preferred of these are a $CF_3(CF_2)_3CH_2CH_2$ group and a $CF_3(CF_2)_5CH_2CH_2$ group.

Preferred as $R^6$, other than the groups substituted with a halogen atom, is a hydrogen atom, a deuterium atom, or an alkyl group having a carbon number of from 1 to 3, which may have been substituted with a deuterium atom. More preferred is a methyl group which may have been substituted with a deuterium atom.

The compound (3) obtained by the present invention is used as a monomeric starting material for synthetic resins for use in various applications including chemical products or coating materials, and is exceedingly useful industrially.

Meanwhile, polymers obtained by using the deuterated unsaturated-acid ester are utilizable as optical fibers usable in high-capacity high-speed transmission systems and the like.

Furthermore, from the compound (3) produced by the present invention, other esters or carboxylic acids may be synthesized by known methods.

Examples of such methods include a method in which water or an alcohol is heated together with the unsaturated-acid ester or unsaturated acid in the presence of a catalytic amount of an acid or base.

In particular, by esterifying the acrylic acid with an alcohol, the corresponding acrylic acid ester is easily obtained.

Reaction

The present invention is characterized in that the reaction is caused to proceed at a given temperature especially in the presence of a Lewis acid catalyst.

The Lewis acid catalyst, reaction conditions, and the like in the present invention are described below in detail.

(Lewis Acid Catalyst)

A Lewis acid catalyst is used in the reaction according to the present invention.

Examples of the Lewis acid catalyst to be used in the present invention include one member selected from the group consisting of compounds represented by the following formula (4) (excluding water) or a mixture of two or more members thereof.

$$M_n Y_m \quad (4)$$

(In formula (4), M is a cation of hydrogen or a metal or metalloid selected from the group consisting of elements of Group 2 and Groups from 4 to 14 of the periodic table, Y is an anion selected from the group consisting of oxide ions, halide ions, a sulfate ion, a nitrate ion, a carbonate ion, a hydrogen carbonate ion, a sulfide ion, a hydroxide ion, alkoxide ions, a phosphate ion, an acetate ion, and a perchlorate ion, and n and m are numbers satisfying (valence of the cation M)×n=(valence of the anion Y)×m.)

From the standpoint of more effectively obtaining an unsaturated-acid ester or unsaturated acid, it is preferable that the M should be a cation of a metal or metalloid selected from the group consisting of zinc, zirconium, silicon, chromium, iron, aluminum, lead, magnesium, indium, cobalt, manganese, and nickel. Especially preferred of these is a cation of a metal or metalloid selected from the group consisting of zinc, silicon, indium, cobalt, manganese, and nickel.

Meanwhile, the Y preferably is an oxide ion.

Other examples of the Lewis acid catalyst to be used in the present invention include solid acids such as an activated clay, an acid clay, a zeolite, a heteropolyacid, or an ion-exchange resin.

The activated clay is a one obtained by treating naturally occurring acid clay (montmorillonite clay) with a mineral acid such as sulfuric acid, and is a compound having a porous structure. The activated clay contains $SiO_2$, $Al_2O_3$, $Fe_2O_3$, CaO, MgO, and the like as components thereof The term zeolite means a class of substances which have a structure formed by replacing some of the silicon (Si) atoms of a substance containing silicon dioxides as the basic framework with aluminum (Al) atoms. Specifically, it means the zeolites provided for by the International Zeolite Association (IZA), and examples thereof include ones at least contain oxygen, aluminum (Al), and phosphorus (P) and ones at least contain oxygen, aluminum, and silicon (Si), as atoms constituting the framework structure.

Heteropolyacids generally are composite oxide acids each constituted of a composite of two or more different oxides and those in which some or all of the protons thereof have been replaced with other cations. A heteropolyacid is configured, for example, of oxoacid ions of an element such as phosphorus, arsenic, tin, silicon, titanium, or zirconium (e.g., phosphoric acid or silicic acid) and oxoacid ions of an element such as molybdenum, tungsten, vanadium, niobium, or tantalum (e.g., vanadic acid, molybdic acid, or tungstic acid). On the basis of combinations thereof, various heteropolyacids are possible.

The elements of the oxoacids which constitute the heteropolyacids are not particularly limited. Examples thereof include copper, beryllium, boron, aluminum, carbon, silicon, germanium, tin, titanium, zirconium, cerium, thorium, nitrogen, phosphorus, arsenic, antimony, vanadium, niobium, tantalum, chromium, molybdenum, tungsten, uranium, selenium, tellurium, manganese, iodine, iron, cobalt, nickel, rhodium, osmium, iridium, and platinum.

Ion-exchange resins are resins which contain as a framework a polymer based on a fluorocarbon, hydrocarbon or the like and into which ion-exchange groups have been introduced. Use can be made of one having, as ion-exchange groups, one or plurality of cation-exchange groups such as sulfonic group, carboxylic group, or phosphate group. Especially desirable is an ion-exchange resin constituted of a perfluorocarbon framework which has chemical resistance and into which sulfonic groups have been introduced as ion-exchange groups. Examples thereof include Flemion, manufactured by Asahi Glass Co., Ltd., and Nafion, manufactured by DuPont.

The Lewis acid catalyst of the present invention may be fixed to a support.

In the case of conducting the reaction in a continuous mode, the kind of the support is not particularly limited. Examples thereof include oxides of either metals or metalloids, salts thereof, and inorganic carbon. Specific examples thereof include silica, alumina, titania, zirconia, zeolites, and activated carbon.

In the case of conducting the reaction in a batch mode, the kind of the support may be the same as in the continuous mode. Specific examples thereof include silica, alumina, titania, and zirconia.

In the case where such supports are Lewis acids, the supports also are capable of functioning as a Lewis acid catalyst.

Preferred as the Lewis acid catalyst or as the Lewis acid catalyst fixed to a support, to be used in the present invention, are $ZnO$—$ZrO_2$, $ZnO$—$Al_2O_3$, $ZnO$—$TiO_2$, $In_2O_3$—

$ZrO_2$, $NiO$—$ZrO_2$, $CoO$—$ZrO_2$, $MnO$—$ZrO_2$, activated carbon, silica gel, γ-alumina, $ZrO_2$, $ZnO$—$SiO_2$, $Zr$—$PbO_x$, $Al_2O_3$—$ZrO_2$, $MgO$—$ZrO_2$, $ZnO$—$Cr_2O_3$, $TiO_2$, and $Zr$—$NiO_x$. More preferred are $ZnO$—$ZrO_2$, $ZnO$—$SiO_2$, $ZrO_2$, $ZnO$—$TiO_2$, $In_2O_3$—$ZrO_2$, $NiO$—$ZrO_2$, $CoO$—$ZrO_2$, and $MnO$—$ZrO_2$. Most preferred are $ZnO$—$ZrO_2$, $ZnO$—$SiO_2$, $ZnO$—$TiO_2$, $In_2O_3$—$ZrO_2$, and $NiO$—$ZrO_2$.

The amount of the catalyst to be used, per 1 mol of the compound (1) present in the reaction vessel in a batch mode or per 1 mol of the compound (1) residing in the reaction vessel in a continuous mode, is preferably from 0.001 to 1 mol, more preferably from 0.01 to 0.2 mol and most preferably from 0.02 to 0.1 mol.

In the case where the amount of the catalyst to be used is regulated so as to be the lower limit or more, the efficiency of the production of an unsaturated-acid ester or unsaturated acid can be improved. In case of regulating so as to be the upper limit or less, the volume efficiency improves.

Although the function mechanism of a Lewis acid catalyst in the present invention has not been entirely elucidated, an example of the function mechanism is presumed to be as shown by the following reaction schemes. Specifically, in the case where TCMP and methanol are used as starting materials to produce MMA by using ZnO as a catalyst, the hydroxyl group of the TCMP interacts with the Zn and MMA is yielded via a three-membered-ring intermediate through dechlorination or the like.

[Chem. 5]

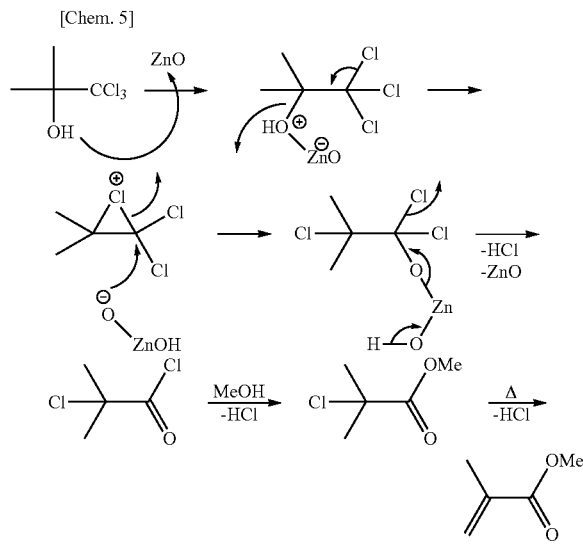

Consequently, in the present invention, the Lewis acid catalyst is not consumed by the reactions as shown by the function mechanism and can hence be reused.

In the case where the catalyst has been deactivated, some or all thereof can be regenerated and used. Examples of regeneration methods include a method of heating in an inert gas or in a gas containing oxygen, a method in which the catalyst is treated with a hydrogen halide gas or with an aqueous solution of a hydrogen halide, and a combination of thereof.

(Reaction Temperature)

The reaction according to the present invention is conducted at a temperature of the boiling point of the compound (1) or higher and 350° C. or lower.

The reaction temperature is suitably set in accordance with the starting-material compounds or the kind of the catalyst.

Specifically, it is preferably from 170 to 350° C. and more preferably from 200 to 300° C.

In the case where the reaction temperature is the lower limit or higher, an unsaturated-acid ester or an unsaturated acid is efficiently obtained. In the case of the upper limit or lower, decomposition of the starting materials and the product and increase of side reactions are less apt to occur.

(Reaction Phase)

According to the present invention, the compound (3) is obtained by conducting the reaction either in a gas phase or in a liquid phase. In the case of conducting in a gas phase, the compound (3) is obtained more efficiently.

Whether the reaction is conducted in a gas phase or a liquid phase depends on the boiling points of the starting materials. However, it can be suitably changed, depending on the setting of the reaction temperature described above or of the reaction pressure described later.

(Solvent or Diluent Gas)

In the reaction according to the present invention, a compound or gas which does not chemically react with the starting materials and reaction products can be used as a solvent or a diluent gas from the standpoints of handling of the starting materials and control of heat of reaction.

Examples of the solvent include pentane, hexane, heptane, petroleum ether, dimethyl ether, diethyl ether, tetrahydrofuran, 1,2-dimethyoxyethane, dichloromethane, chloroform, carbon tetrachloride, dichloroethane, acetic acid, benzoic acid, acetic anhydride, ethyl acetate, acetone, 2-butanone, acetonitrile, dimethylformamide, dimethylacetamide, dimethyl sulfoxide, benzene, toluene, chlorobenzene, dichlorobenzene, benzonitrile, nitromethane, nitrobenzene, and mixtures thereof Examples of the diluent gas include nitrogen, helium, argon, and mixtures thereof. Nitrogen is preferred of these because it is easily available and is inexpensive.

The amount of the solvent or diluent gas to be used is preferably in such a range that the concentration of the compound (1) is kept at 5% by mass or higher, and more preferably at 10% by mass or higher.

In the case where the concentration of the compound (1) is regulated so as to be the lower limit or more, an unsaturated-acid ester or an unsaturated acid can be more efficiently produced.

(Reaction Mode)

The reaction mode of the present invention may be a batch mode or a continuous mode. In adopting either mode, the effects of the present invention can be obtained.

In the case of conducting in a continuous mode, the space velocity is preferably from 1 to 500,000 h$^{-1}$, more preferably from 100 to 50,000 h$^{-1}$, and most preferably from 100 to 10,000 h$^{-1}$.

In this description, the term "space velocity" is mass space velocity per unit mass of the catalyst, and is a value obtained by dividing the flow rate (kg/h) of the compound (1) by the mass (kg) of the catalyst including a support or the like. Incidentally, the reciprocal of the space velocity is called contact time or residence time.

(Reaction Pressure)

It is preferable that the reaction pressure should be suitably regulated in accordance with the vapor pressures of the compound (1), the solvent, and other gases. It may be either an elevated pressure or a reduced pressure. It is more preferably from 0 MPa to 10 MPa, even more preferably from 0.05 MPa to 2 MPa, and most preferably from 0.1 MPa to 1 MPa, in terms of absolute pressure.

(Reaction Time)

The reaction time can be suitably set in accordance with various conditions including the catalyst and the temperature.

For example, in the case of conducting in a batch mode, it is preferably from 10 minutes to 12 hours and more preferably from 30 minutes to 3 hours.

In the case of conducting in a continuous mode, it is preferably from 0.1 second to 60 minutes and more preferably from 0.5 seconds to 30 minutes. Especially in the case of conducting in a continuous mode in a gas phase, it is preferably from 0.5 seconds to 30 seconds. In the case of a continuous mode, the reaction time is also called contact time or residence time.

Alternatively, while the reaction is being allowed to proceed, some of the crude reaction liquid is taken out and examined by gas chromatography or the like to determine the concentration of a reaction product, and the yielded amount is presumed from the concentration, and at the time when the reaction product has been yielded in a desired amount, the reaction may be terminated.

(By-Products of the Reaction)

In the present invention, a hydrogen halide (including a deuterium halide) is obtained as one of by-products of the reaction.

The hydrogen halide can be utilized in various applications.

For example, it can serve as a starting material for vinyl halides, halogenated methanes or other alkyl halides, aryl halides, halogen gases, or metal halides. Further, in the case where a halogenated methane or the halogen gas is obtained, it can be recycled as a starting material for synthesizing the compound (1).

Since a hydrogen halide, which is a strong acid, is yielded as a by-product in the reaction according to the present invention, it is preferable that a reactor used in the present invention should be one which can withstand strong acids.

Examples include iron, chromium, nickel and alloys containing these as main components, quartz, glass, glass linings, fluororesins such as ethylene/tetrafluoroethylene copolymers (ETFE), or fluororesin linings. Preferred from the standpoint of corrosion resistance are nickel-chromium alloys such as Hastelloy, Inconel and Carpenter, glass, or fluororesins.

Purification of Compound (3)

In the present invention, the compound (3) obtained by the reaction may be purified.

Examples of methods for purifying the compound (3) include distillation, crystallization, sublimation, washing with a liquid, filtration, or combinations of these.

In the present invention, purification by distillation or crystallization is preferred, and distillation is more preferred.

The distillation can be conducted by a known method.

Examples of distillation columns include general distillation columns such as sieve trays, dual trays, bubble-cap trays, Sulzer packings, Technopack, Mellapak, Raschig rings, Pall rings, Cascade Mini Ring, or a combination of these.

In the distillation, a polymerization inhibitor may be added.

Examples of the polymerization inhibitor include hydroquinone (HQ), monomethyl ether of hydroquinone (MEHQ), phenothiazine (PTZ), hindered-amine radical scavenger compounds, or catechols such as tertiary butyl-catechol or di-tertiary butylcatechol. To cause an oxygen-containing gas to be present is also effective for inhibiting the polymerization. Furthermore, metals containing copper also can inhibit the polymerization.

In the case where no polymerization inhibitor is added, it is preferred to select a distillation column of the type which contains few portions where stagnation occurs, from the standpoint of preventing unintended polymerization.

With respect to the temperature and pressure in the distillation operation, conditions in common use in the distillation of unsaturated acids or esters thereof may be employed. For example, a temperature not exceeding 80° C. is selected in order to inhibit polymerization in the column bottom part, and a vapor pressure is determined in accordance with the set temperature.

The crystallization also can be conducted by a known method.

Crystallization is an operation in which a component of a solution is crystallized out by cooling, heating, depressurization, or the like while utilizing the temperature or pressure dependence of solubility, to achieve selective isolation.

In the case where the reaction product according to the present invention is MMA, this is often obtained as a mixture with methanol. It is known that these compounds form an azeotrope.

In such cases, there may be mentioned, for example, a method in which the MMA and the methanol are recovered by using a method in which a distillation is conducted with using an azeotropic solvent or a method in which they are separated by utilizing layer separation (JP-A-H11-124347).

Since impurities can be removed by purification, the unsaturated-acid ester or unsaturated acid obtained by the present invention comes to be usable in a wider range of applications and it becomes possible to produce therefrom polymeric materials which have better heat resistance and transparency, are colorless, and have high quality.

(Effects)

According to the present invention, an unsaturated-acid ester or an unsaturated acid can be produced on an industrial scale without using a large amount of a chemical such as a basic compound. In particular, in the case where the reaction according to the present invention is conducted in a gas phase, the unsaturated-acid ester or unsaturated acid can be efficiently produced.

In the present invention, in the case of using an alcohol as compound (2), an unsaturated-acid ester is apt to be efficiently obtained, and in the case of using water, an unsaturated acid is apt to be efficiently obtained.

The Lewis acid catalyst used in the present invention can be reused.

According to the present invention, a by-product yielded from the halogen moiety of a starting material can be obtained as a hydrogen halide which is easy to utilize effectively.

EXAMPLES

The method of the present invention for producing an unsaturated-acid ester or an unsaturated acid is described below in detail by reference to Examples. However, the present invention should not be construed as being limited to the following Examples.

Example 1

A catalyst constituted of 5% by mass zirconium-supported zinc oxide (5% ZnO—$ZrO_2$) was obtained by an impregnation method.

Into a glass tube having a length of 30 cm and an inner diameter of 14 mm was packed 8.2 g of the 5% ZnO—ZrO$_2$ catalyst. The temperature was kept at 200° C.

While nitrogen gas was being fed to the glass tube at a flow rate of 0.05 L/min, a TCMP 0.5-hydrate dissolved in methanol at 50% by mass was fed thereto at a flow rate of 10.0 g/hr to conduct a reaction in a gas phase. In this Example, 26.5 g of the 50% by mass methanol solution of TCMP 0.5-hydrate, that is, 12.6 g (0.071 mol) of TCMP was fed. The amount of the TCMP used is expressed by X (mol).

The gas obtained by the reaction was cooled with dry ice to obtain a crude reaction liquid. In this Example, 22.6 g of the crude reaction liquid was obtained. The amount of the crude reaction liquid obtained is expressed by W (g).

The concentration of MMA, Z (mol/g), in the crude reaction liquid was determined by gas chromatography by using dichloromethane as an internal reference.

The total amount T (mol) of the MMA obtained by the reaction was calculated by using the equation $T = Z \times W$.

The yield Y (%) of the MMA was calculated by using the equation $Y = (T/X) \times 100$.

Examples 2 to 15

In Examples 2 to 15, crude reaction liquids were obtained by conducting reactions in the same manner as in Example 1, except that the kind of catalyst, catalyst packing amount, reaction temperature, flow rates of the TCMP solution and nitrogen gas, solution amount and amount X (mol) of the TCMP used were changed as shown in Table 1. The concentration of MMA, Z (mol/g), in each crude reaction liquid was determined.

The total amount T (mol) of the MMA in each crude reaction liquid obtained, W (g), and the yield Y (%) of the MMA were calculated in the same manners as in Example 1.

Comparative Example 1

In a 50-mL eggplant type flask equipped with a Dimroth condenser, 1.4 g of a 5% ZnO—ZrO$_2$ catalyst obtained by an impregnation method in the same manner as in Example 1 was prepared.

Thereto were added 3.0 g (16.9 mmol) of TCMP and 0.5 g (16.9 mmol) of methanol.

The contents were stirred with a stirrer at 140° C. for 1 hour to conduct a reaction in a liquid phase.

After the stirring, the contents were cooled to room temperature, and the catalyst was removed.

In this Comparative Example, 3.47 g of crude reaction liquid was obtained.

In the same manners as in Examples 1 to 15, the concentration of MMA, Z (mol/g), in the crude reaction liquid was determined and the total amount T (mol) and yield Y (%) of the MMA obtained in this Comparative Example were calculated.

In Table 2 are shown the amounts W (g) of the crude reaction liquids obtained, the amounts T (mol) of the MMA produced, and the yields Y (%) of the MMA based on the TCMP, as results of Examples 1 to 15 and Comparative Example 1.

TABLE 1

| | | Catalyst | | Reaction temperature (° C.) | Flow rate of TCMP solution (g/hr) | Flow rate of N$_2$ (L/min) | Amount of TCMP solution (g) | Amount of TCMP in the solution X (mol) ×10$^2$ |
|---|---|---|---|---|---|---|---|---|
| | | Kind | Amount packed (g) | | | | | |
| Example | 1 | 5% ZnO—ZrO$_2$ | 8.2 | 200 | 10.0 | 0.05 | 26.5 | 7.10 |
| | 2 | 5% ZnO—ZrO$_2$ | 8.9 | 250 | 10.0 | 0.05 | 28.2 | 7.56 |
| | 3 | 10% ZnO—ZrO$_2$ | 9.5 | 250 | 2.8 | 0.10 | 11.3 | 3.03 |
| | 4 | silica gel | 3.8 | 250 | 2.8 | 0.05 | 9.0 | 2.41 |
| | 5 | γ-alumina | 7.3 | 250 | 10.5 | 0.05 | 32.4 | 8.69 |
| | 6 | ZrO$_2$ | 8.3 | 250 | 2.8 | 0.10 | 11.3 | 3.03 |
| | 7 | ZnO—SiO$_2$ | 9.5 | 200 | 10.0 | 0.05 | 26.4 | 7.08 |
| | 8 | Zr•PbO$_x$ | 12.4 | 200 | 10.0 | 0.05 | 25.9 | 6.94 |
| | 9 | MgO—ZrO$_2$ | 10.0 | 250 | 10.5 | 0.05 | 32.4 | 8.69 |
| | 10 | ZnO—Cr$_2$O$_3$ | 10.0 | 250 | 2.8 | 0.10 | 11.1 | 2.98 |
| | 11 | Zr—NiO$_x$ | 12.2 | 250 | 2.7 | 0.10 | 11.0 | 2.95 |
| | 12 | 1.6% In$_2$O$_3$—ZrO$_2$ | 11.6 | 200 | 10.0 | 0.05 | 24.9 | 7.02 |
| | 13 | 10% NiO—ZrO$_2$ | 6.4 | 200 | 10.0 | 0.05 | 25.3 | 7.13 |
| | 14 | 10% CoO—ZrO$_2$ | 6.5 | 200 | 10.0 | 0.05 | 24.7 | 6.96 |
| | 15 | 10% MnO—ZrO$_2$ | 6.4 | 200 | 10.0 | 0.05 | 24.4 | 6.87 |
| Comparative Example 1 | | 5% ZnO—ZrO$_2$ | 1.4 | 140 | — | — | 3.5 | 1.69 |

TABLE 2

| | | Crude reaction liquid W (g) | MMA concentration of crude reaction liquid Z (mol/g) ×10$^3$ | Amount of MMA produced T (mol) ×10$^2$ | Yield of MMA Y (%) |
|---|---|---|---|---|---|
| Example | 1 | 22.6 | 2.27 | 5.14 | 72.3 |
| | 2 | 20.0 | 2.66 | 5.31 | 70.2 |
| | 3 | 6.2 | 2.06 | 1.28 | 42.3 |
| | 4 | 6.1 | 0.16 | 0.097 | 4.0 |
| | 5 | 30.0 | 0.14 | 0.42 | 4.8 |
| | 6 | 8.9 | 0.47 | 0.42 | 13.9 |
| | 7 | 19.4 | 2.35 | 4.56 | 64.4 |
| | 8 | 25.1 | 0.07 | 0.18 | 2.6 |
| | 9 | 31.7 | 0.07 | 0.23 | 2.6 |
| | 10 | 9.0 | 0.41 | 0.37 | 12.4 |

TABLE 2-continued

|  | Crude reaction liquid W (g) | MMA concentration of crude reaction liquid Z (mol/g) ×10³ | Amount of MMA produced T (mol) ×10² | Yield of MMA Y (%) |
|---|---|---|---|---|
| 11 | 9.2 | 0.26 | 0.24 | 8.1 |
| 12 | 21.7 | 2.21 | 4.80 | 74.5 |
| 13 | 21.7 | 1.82 | 3.96 | 60.2 |
| 14 | 22.6 | 1.51 | 3.41 | 48.0 |
| 15 | 22.6 | 0.99 | 2.24 | 35.8 |
| Comparative Example 1 | 3.47 | 0.04 | 0.012 | 0.7 |

The results given above showed that MMA was obtained in sufficient yields in Examples 1 to 15, in which the reactions were conducted at high temperatures by using Lewis acid catalysts.

Namely, it was demonstrated that according to the present invention, MMA is obtained in one step from TCMP and methanol as starting materials.

Relatively high yields of MMA were obtained especially in Examples 1 to 3, 7, and 12 to 15, in which $ZnO$—$ZrO_2$, $ZnO$—$SiO_2$, $In_2O_3$—$ZrO_2$, $NiO$—$ZrO_2$, $CoO$—$ZrO_2$, and $MnO$—$ZrO_2$ were used as the catalysts. In particular, Examples 1 to 3, 7, 12, and 13, in which $ZnO$—$ZrO_2$, $ZnO$—$SiO_2$, $In_2O_3$—$ZrO_2$, and $NiO$—$ZrO_2$ were used, gave remarkably high yields.

On the other hand, in Comparative Example 1, in which the reaction was conducted at 140° C., MMA was not sufficiently obtained.

The causes of the results that the yields of MMA in Examples 1 to 15 were far higher than that in Comparative Example 1 include the difference between Examples 1 to 15 and Comparative Example 1 in whether the reaction was conducted in a gas phase or a liquid phase.

In the case where the reaction is conducted in a liquid phase, it is highly probable that the methanol functions as a Lewis base and combines with the Lewis acid catalyst to deprive the catalyst of its function.

On the other hand, in the case where the reaction is conducted in a gas phase, the methanol gasifies and is hence present in a low concentration in the field of reaction and less apt to deactivate the Lewis acid catalyst. It is hence thought that the catalytic reaction proceeds easily and MMA is produced in a high yield.

Consequently, when the reaction according to the present invention is conducted in a gas phase, a methacrylic acid ester is obtained more efficiently.

It has been concluded that by setting the reaction temperature to 170° C. or higher in view of the boiling point of TCMP of 169° C., the effects of the present invention are further enhanced.

Example 16

In this Example, TCMP and water were used as starting materials to be reacted and the reaction was conducted at 200° C.

Into a metallic tube (manufactured by Morimoto Seikan) made of Hastelloy C-276 and having a length of 20 cm and an inner diameter of 21.3 mm was packed 43.12 g of a 5% $ZnO$—$TiO_2$ catalyst obtained by an impregnation method in the same manner as in Example 1. The temperature was kept at 200° C.

In this Example, the starting materials were gasified beforehand in order to more efficiently conduct the reaction. Specifically, a metallic tube (preheating tube) made of Hastelloy C-276 and heated at 200° C. was prepared separately from the reaction tube, and a TCMP dissolved in chloroform at 85% by weight and water were fed to the preheating tube at flow rates of 57.3 g/hr and 4.9 g/hr, respectively, and gasified. The resultant gas was mixed with nitrogen being supplied at 29.5 mL/min, and then fed to the reaction tube and allowed to react for 3 hours. The amount of the 85% by mass chloroform solution of TCMP fed was 164.5 g, and the amount of the water fed was 13.3 g.

The gas obtained by the reaction was cooled with dry ice to obtain 114.7 g of a crude reaction liquid. The hydrogen chloride gas yielded as a by-product was absorbed with caustic potash and recovered.

The concentration of MAA in the crude reaction liquid was determined by gas chromatography by using dichloromethane as an internal reference.

The total amount and yield of the MAA and the amount of hydrogen chloride were calculated in the same manners as in Examples 1 to 15.

As a result, the yield of the MAA was 70.1%, and hydrogen chloride was recovered in an amount of 55.01 g. The recovery rate of the hydrogen chloride based on a theoretical value was 74.6%.

Comparative Example 2

In this Comparative Example, a reaction was conducted in the same manner as in Comparative Example 1, except that water was used in an amount of 0.3 g (16.9 mmol) in place of the methanol as a starting material to be reacted In this Comparative Example, 3.47 g of a crude reaction liquid was obtained.

In Examples 1 to 3 and 16 and Comparative Example 2, the concentrations of MAA in the crude reaction liquids were determined by gas chromatography using dichloromethane as an internal reference, and the yields of the MAA were calculated.

In Table 3 are shown the yields of the MAA in Examples 1 to 3 and 16 and Comparative Example 2.

TABLE 3

|  |  | Yield of MAA (%) |
|---|---|---|
| Example | 1 | 6.7 |
|  | 2 | 7.5 |
|  | 3 | 6.7 |
|  | 16 | 70.1 |
| Comparative Example 2 |  | 0.31 |

The results given above demonstrated that according to the present invention, MAA is obtained in one step from TCMP and either methanol or water as starting materials.

In particular, it was shown that when water is used a starting material to conduct the reaction in a gas phase, MAA is efficiently obtained.

Example 17

In this Example, mass-production of MMA by the present invention was investigated.

Into a metallic tube (manufactured by Morimoto Seikan K.K.) made of Hastelloy C-276 and having a length of 30 cm and an inner diameter of 21.3 mm (reaction tube) was packed 77.5 g of a 5% $ZnO$—$ZrO_2$ catalyst obtained by an impregnation method in the same manner as in Example 1. The temperature was kept at 200° C.

In this Example, the starting materials were gasified before being fed to the reaction tube in order to more efficiently conduct the reaction. Specifically, a metallic tube (preheating tube) made of Hastelloy C-276 and heated at 170° C. was prepared separately from the reaction tube, and a TCMP dissolved in acetone at 85% by mass and methanol were fed to the preheating tube at flow rates of 13.17 g/hr and 16.9 g/hr, respectively, and gasified. The resultant gas was mixed with nitrogen being supplied at 27.4 mL/min, and then fed to the reaction tube. The reaction was conducted for 11.5 hours. The amount of the 85% by mass acetone solution of TCMP fed was 155.5 g, and the amount of the methanol fed was 187.6 g.

The gas obtained by the reaction was cooled with an ice bath to obtain a crude reaction liquid. Furthermore, in order to collect the chloromethane obtained by the reaction of the by-product hydrogen chloride with the methanol, the gas was cooled with dry ice to collect the by-product gas. In this Example, 216.0 g of the crude reaction liquid and 113.2 g of the chloromethane were obtained.

The concentration of MMA in the crude reaction liquid was determined by gas chromatography by using tetraethylene glycol dimethyl ether as an internal reference.

The total amount and yield of the MMA were calculated in the same manners as in Examples 1 to 16.

As a result, the yield of the MMA was 93.9%, and it was ascertained that the hydrogen chloride which was yielded as a by-product of the reaction has been substantially wholly converted to chloromethane.

Namely, the results of this Example show that the method of the present invention is a method capable of producing MMA on an industrial scale.

While the present invention has been described in detail and with reference to specific embodiments thereof, it will be apparent to one skilled in the art that various changes and modifications can be made therein without departing from the spirit and scope thereof.

The present application is based on Japanese Patent Application No. 2013-146864, which was filed on Jul. 12, 2013, the contents thereof being incorporated herein by reference.

The invention claimed is:

1. A method for producing an unsaturated-acid ester or an unsaturated acid, the method comprising
reacting a compound (1) of the formula (1) with a compound (2) of the formula (2), which is different from the compound of the formula (1), in the presence of a Lewis acid catalyst at a temperature within a range from 170° C. to 350° C., thereby obtaining a reaction product comprising a compound (3) of the formula (3)

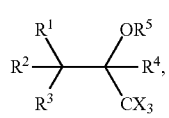 (1)

wherein $R^1$, $R^2$, and $R^4$ each independently are selected from the group consisting of a hydrogen atom, a deuterium atom, and an alkyl group which has a carbon number of from 1 to 3 and may be optionally substituted with a halogen atom and/or a deuterium atom, $R^3$ and $R^5$ each independently are selected from the group consisting of a hydrogen atom and a deuterium atom, and X is a chlorine atom, a fluorine atom, a bromine atom, or an iodine atom;

 (2), wherein $R^6$ is selected from the group consisting of a hydrogen atom, a deuterium atom, and an alkyl group which has a carbon number of from 1 to 11 and may be optionally substituted with a halogen atom and/or a deuterium atom, or an aryl group and may be optionally substituted with a halogen atom and/or a deuterium atom, and $R^7$ is a hydrogen atom or a deuterium atom; and

 (3)

wherein $R^1$, $R^2$, and $R^4$ are the same as defined with regard to the formula (1), and $R^6$ is the same as defined with regard to the formula (2); wherein the Lewis acid catalyst is at least one selected from the group consisting of $ZnO$—$ZrO_2$, $ZnO$—$Al_2O_3$, $ZnO$—$TiO_2$, $In_2O_3$—$ZrO_2$, $NiO$—$ZrO_2$, $CoO$—$ZrO_2$, $MnO$—$ZrO_2$, silica gel, γ-alumina, $ZrO_2$, $ZnO$—$SiO_2$, $Zr$ $PbO_x$, $Al_2O_3$—$ZrO_2$, $MgO$—$ZrO_2$, $ZnO$—$Cr_2O_3$, $TiO_2$, and $Zr$—$NiOx$, and wherein the Lewis acid catalyst is fixed to a support.

2. The method according to claim 1, wherein the Lewis acid catalyst is a solid acid.

3. The method according to claim 1, wherein the reaction is conducted in a gas phase.

4. The method according to claim 1, wherein an amount of the compound (2) is from 0.5 to 20 mol, per 1 mol of the compound (1).

5. The method according to claim 1, wherein an amount of the compound (2) is from 1 to 10 mol, per 1 mol of the compound (1).

6. The method according to claim 1, wherein an amount of the Lewis acid catalyst, per 1 mol of the compound (1) present in a reaction vessel, is from 0.001 to 1 mol.

7. The method according to claim 1, wherein an amount of the Lewis acid catalyst, per 1 mol of the compound (1) present in a reaction vessel in a batch mode or per 1 mol of the compound (1) residing in a reaction vessel in a continuous mode, is from 0.01 to 0.2 mol.

8. The method according to claim 1, wherein the reacting temperature is from 200 to 300° C.

9. The method according to claim 1, wherein the reaction is conducted in a liquid phase.

10. The method according to claim 1, wherein in the reaction a compound or gas which does not chemically react with starting materials and the reaction product is used as a solvent or a diluent gas,
wherein the solvent is selected from the group consisting of pentane, hexane, heptane, petroleum ether, dimethyl ether, diethyl ether, tetrahydrofuran, 1,2-dimethyoxyethane, dichloromethane, chloroform, carbon tetrachloride, dichloroethane, acetic acid, benzoic acid, acetic anhydride, ethyl acetate, acetone, 2-butanone, acetonitrile, dimethylformamide, dimethylacetamide, dimethyl sulfoxide, benzene, toluene, chlorobenzene, dichlorobenzene, benzonitrile, nitromethane, nitrobenzene, and a mixture thereof, and wherein the diluent gas is selected from the group consisting of nitrogen, helium, argon, and a mixture thereof.

11. The method according to claim 10, wherein an amount of the solvent or the diluent gas is in a range that a concentration of the compound (1) is kept at 5% by mass or higher.

12. The method according to claim 1, wherein the reaction is conducted in a continuous mode and a space velocity is from 1 to 500,000 $h^{-1}$.

13. The method according to claim 1, wherein a reaction pressure is from 0 MPa to 10 MPa.

14. The method according to claim 1, wherein a reaction pressure is from 0.05 MPa to 2 MPa.

15. The method according to claim 1, wherein when the reacting is conducted in a batch mode, a reaction time is from 10 minutes to 12 hours, and when the reacting is conducted in a continuous mode, a reaction time is from 0.1 second to 60 minutes.

* * * * *